United States Patent [19]

Watabe

[11] Patent Number: 5,215,097
[45] Date of Patent: Jun. 1, 1993

[54] SPHYGMOMETER FOR DETERMINING A PULSE RATE IN COMBINATION WITH A PEN

[75] Inventor: Yusaku Watabe, Atsugi, Japan

[73] Assignee: Winners Japan Company Limited, Tokyo, Japan

[21] Appl. No.: 759,801

[22] Filed: Sep. 5, 1991

Related U.S. Application Data

[63] Continuation-in-part of Ser. No. 552,685, Jul. 11, 1990.

[30] Foreign Application Priority Data

Jul. 17, 1989 [JP] Japan ................. 1-83104[U]

[51] Int. Cl.$^5$ .............................. A61B 5/02
[52] U.S. Cl. ........................ 128/689; 128/680; 128/681; 128/687; 128/695; 128/709; 128/713
[58] Field of Search ............... 128/680, 681, 686, 687, 128/689, 690, 691, 693, 709, 710, 713, 714

[56] References Cited

U.S. PATENT DOCUMENTS

| | | | |
|---|---|---|---|
| 4,185,621 | 1/1980 | Morrow | 128/690 X |
| 4,305,401 | 12/1981 | Reissmueller | 128/690 |
| 4,867,170 | 9/1989 | Takahashi | 128/690 |

Primary Examiner—Stephen C. Pellegrino
Assistant Examiner—Jeffrey A. Schmidt
Attorney, Agent, or Firm—Wenderoth, Lind & Ponack

[57] ABSTRACT

A sphygmometer digitally displays a pulse rate merely by bringing a sensor into contact with skin covering an artery. The sphygmometer includes a main body, pulse sensing device for sensing pulse in such a manner that the pulse sensing device is directly or indirectly brought in contact with skin covering an artery, a display provided in the main body for digitally displaying pulse data and a microcomputer provided in the main body for arithmetically computing the pulse rate per minute on the basis of pulses in predetermined seconds sensed by the pulse sensing device and transmitting a signal corresponding to the computer pulse rate to the display.

16 Claims, 4 Drawing Sheets

SPHYGMOMETER FOR DETERMINING A PULSE RATE IN COMBINATION WITH A PEN

This application is a continuation-in-part of now abandoned application, Ser. No. 07/552,685, filed Jul. 11, 1990, now abandoned.

BACKGROUND OF THE INVENTION

The present invention relates to a sphygmometer, and more particularly to a sphygmometer in which a pulse rate can be digitally displayed merely by bringing a sensing means into contact with skin covering an artery.

Heretofore, the pulse rate of a patient has been measured by a method in which a doctor or a nurse places his or her fingertip onto the skin covering a wristbone artery of the patient while clocking a predetermined amount of time. Alternatively, the pulse rate has been measured by a method in which a cuff of a sphygmomanometer is wrapped around an arm of the patient and a stethoscope is inserted underneath the cuff to listen to the pulse.

However, in the conventional method of taking a pulse using a fingertip, the doctor or a nurse is inconvenienced by the need to count the pulse while observing a watch. Further, because the pulse is taken for 10 or 15 seconds and then multiplied by a factor yielding a pulse/min count, inevitable error is generated. Furthermore, in case of a patient with a weak pulse pressure, the doctor or a nurse may not be able to feel the pulse, and thus the pulse rate cannot be measured accurately.

On the other hand, when checking the pulse with the stethoscope, the doctor or a nurse must carry the stethoscope to each hospital room. This may be troublesome due to the shape and size of the stethoscope.

SUMMARY OF THE INVENTION

It is an object of the present invention to provide a sphygmometer which easily can be carried, and one with which anyone can easily and accurately measure a pulse rate.

According to the present invention, there is provided a sphygmometer for measuring a pulse rate comprising a main body, pulse sensing means for sensing a pulse in such a manner that the pulse sensing means is directly or indirectly brought into contact with skin covering an artery, the pulse sensing means being provided in the main body, display means provided in the main body for digitally displaying pulse data, and a microcomputer provided in the main body for arithmetically computing a pulse rate per minute on the basis of the number of pulses sensed by the pulse sensing means in a predetermined number of seconds and transmitting a signal corresponding to the computed pulse rate to the display means.

In accordance with a further aspect of the present invention there is provided a sphygmometer including a main body having an elongated cylindrical shape. The main body is divided into two sections, namely a pen section and a measuring section. These two sections are separated at a boundary substantially at a central position in the lengthwise direction of the main body. The pen section has therein a pen, for example a ballpoint pen, and the measuring section has therein a pulse measuring device including the above mentioned pulse sensing means, display means and microcomputer.

With the above structure, when measuring a pulse rate, the pulse sensing means is directly or indirectly brought into contact with skin covering an artery. The pulses are sensed by the pulse sensing means, the pulse rate per minute is arithmetically computed by the microcomputer on the basis of the number of pulses sensed by the pulse sensing means in the predetermined number of seconds, and a signal corresponding to the computed pulse rate is transmitted to the display means where the pulse rate is digitally displayed. In one preferred embodiment, the pulse sensing means comprises a sound sensor, the sounds of the pulses are detected by the sound sensor, and the detected signals are amplified by an amplifier and then transmitted to the microcomputer. In accordance with a program stored in the microcomputer, the number of pulse sounds counted up to a particular time instant, e.g. twelve pulse sounds when ten seconds have elapsed, is converted to the pulse rate per minute, i.e. 72. The latter number is digitally displayed, e.g. by a liquid crystal digital display.

In the embodiment of the invention wherein the main body is divided into the pen section and the measuring section, after the sphygmometer has been employed for measuring the pulse rate of a patient, a nurse or doctor then can use the device as a pen for making necessary notations. For example, the sphygmometer of the invention can be shifted from one hand to the other and can serve alternately to measure a patient's pulse rate and then to make notations regarding such data.

The above and other objects, features and advantages of the present invention will become apparent from the following description when taken in conjunction with the accompanying drawings in which a preferred embodiment of the present invention is shown by way of illustrative example.

DETAILED DESCRIPTION OF THE PREFERRED EMBODIMENTS

A sphygmometer according to one embodiment of the present invention will be described below with reference to FIGS. 1 through 3.

Figure 1:
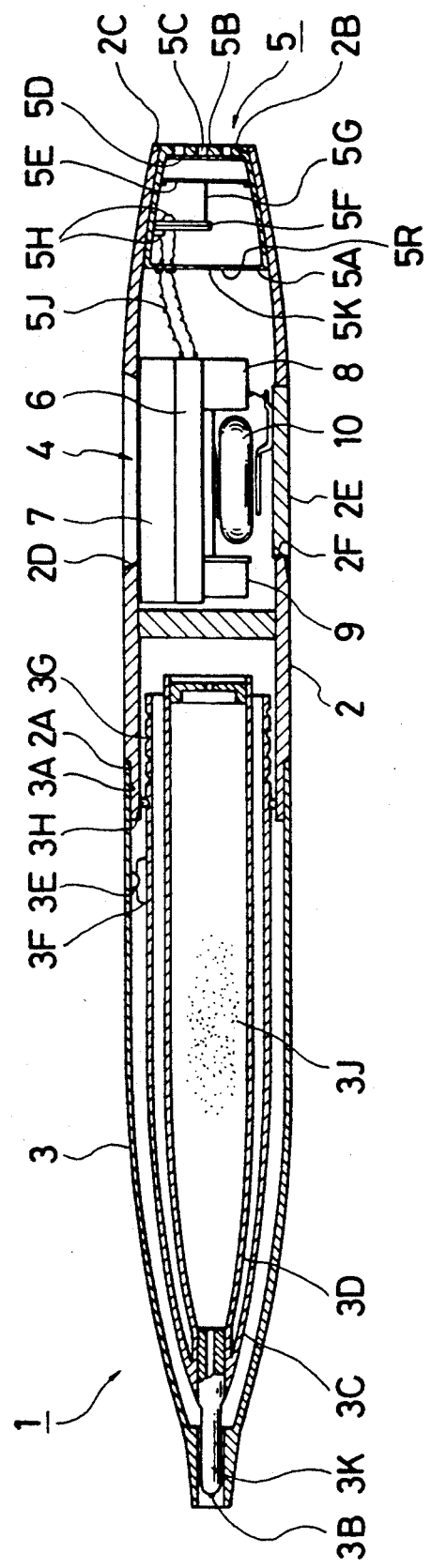
FIG. 1 is a cross-sectional view of a sphygmometer according to an embodiment of the present invention.

In FIG. 1, a sphygmometer 1 has first and second main body sections 2, 3 which together form a main body having an elongate cylindrical shape. The first main body section 2 serves as a measuring section and the second main body section 3 serves as a pen section. The end portions of the first and second main body sections 2, 3 are rotatably and removably connected with each other by a socket and spigot joint 2A, 3A.

The first main body section 2 is formed at a forward end portion thereof with an opening 2B and a circular contacting portion 2C to be contacted with skin of a person. The first main body section 2 is also formed at an intermediate portion thereof with an opening which constitutes a display portion 2D. Further, the first main body section 2 has a battery inlet 2F at a side opposite the display portion 2D and switch portions 2G at a side between the battery inlet 2F and the display portion 2D (see FIG. 3). The battery inlet 2F is removably covered with a lid 2E.

A pulse measuring device 4 is provided in the first main body section 2. The pulse measuring device 4 comprises a pulse sensor 5 constituting pulse sensing means, a microcomputer 6, a digital display 7 of the liquid crystal type (hereinafter referred to as liquid crystal digital display), a plurality of switches 8, timer 9 and a battery 10. The pulse sensor 5 includes a cylindrical case 5A having a front end plate 5B with a plurality of vent holes 5C. A sound resistor or diaphragm 5D is provided, in a stretched state, at a backside of the front end plate 5B. A vibration plate or diaphragm 5E is also provided, in a stretched state, inwardly of and parallel to the sound resistor 5D. Further, inwardly of the vibration plate 5E, a bimorph piezoelectric element 5F is provided in a cantilever fashion, and a tip end of the bimorph piezoelectric element 5F is connected to the vibration plate 5E by a rod 5G. On opposite sides of the bimorph piezoelectric element 5F are provided terminals 5H which are connected to the microcomputer 6 through lead wires 5J. The cylindrical case 5A has rear end plate 5R with a hole 5K for adjusting internal pressure on the basis of atmospheric pressure.

The microcomputer 6 has an input/output (I/O) port 6C to which the pulse sensor 5, the liquid crystal digital display 7, switches 8 and a timer 9 are connected. More particularly, FIG. 2 is a block diagram of pulse measuring device 4. The lead wires 5J from the bimorph piezoelectric element 5F are connected to an amplifier 6D which is connected to a counter 6E. The counter 6E is further connected to a comparator 6F which is connected to the I/O port 6C. The timer 9 which comprises a crystal oscillator 9A and a frequency divider 9B is connected to the counter 6E. The liquid crystal digital display 7 is divided into two sections including a pulse display section 7A and a timer display section 7B.

With the above structure, the pulse sensor 5 is accommodated in the contacting portion 2C and is exposed and positioned in the same plane as the opening 2B that is radially inwardly of the contacting portion 2C, as shown in FIG. 1. The liquid crystal digital display 7 is accommodated in the first main body section 2 in such a manner that the display face thereof is observed through the display portion 2D. The microcomputer 6 is disposed beneath or inwardly of the liquid crystal digital display 7.

The switch mechanism 8 comprises switch buttons 8A to 8H (FIG. 3) which are positioned in an exposed manner at the switch portions 2G. After removing the lid 2E, the battery 10 is inserted through the battery inlet 2F into the first main body section 2 and is loaded at a predetermined position therein. The timer 9 is disposed adjacent to the microcomputer 6.

Next, operation of the sphygmometer 1 thus constructed will be described below.

After turning on a power switch 8A, the contacting portion 2C of the first main body 2 of the sphygmometer 1 is placed onto the skin covering the wristbone artery of a person whose pulse is checked. The beats or sound of the pulse in the artery pass through the vent holes 5C of the cylindrical case 5A and cause the vibration plate 5E to vibrate. The vibration of the vibration plate 5E is immediately transmitted to the bimorph piezoelectric element 5F through the rod 5G, thereby generating covibration of the bimorph piezoelectric element 5F. The covibration of the bimorph piezoelectric element 5F causes the terminals 5H to generate voltage signals. The voltage signals of the bimorph piezoelectric element 5F enter the amplifier 6D through the lead wires 5J where they are amplified by the amplifier 6D and then they are counted at the counter 6E. Thereafter, the voltage signals enter the comparator 6F.

On the other hand, timer pulse signals produced by the crystal oscillator 9A of timer 9 are subjected to frequency division in the frequency divider 9B to provide timer pulse signals having a period of 0.1 second. The resultant pulse signals are fed to the counter 6E where the number of the pulse signals being fed are counted.

Comparator 6F compares the voltage signals of the measured pulse with the timer pulse signals, whereupon the comparison result is processed by a CPU 6A in accordance with a program stored in a memory 6B. Numerals indicative of elapse of time in seconds are digitally displayed on the timer display section 7B, and the number of pulses counted by counter 6E is digitally displayed on the pulse display section 7A as time elapses. That is, when elapsed time is 2 or 3 seconds, numeral 2 or 3 is displayed on the timer display section 7B, and the number of counted pulses, for example, 2, 3 or 4, is displayed on the pulse display section 7A.

Next, when a conversion switch button 8B is depressed, the number of the person's pulses counted to that instant, e.g. twelve at a time when ten seconds have elapsed, is converted to the number of the person's pulses (the pulse rate) in one minute, i.e. 72. The latter numeral is displayed on the pulse display section 7A. In the timer display section 7B, numeral "60" is displayed to indicate that the number of the person's pulses on the pulse display section 7A is for 60 seconds or one minute.

When a memory switch button 8C is depressed, the pulse rate per one minute (72) is stored in the memory 6B as an average.

Next, after depressing an irregular pulse switch button 8D, the contacting portion 2C is pressed onto the skin covering the wristbone artery for pulse measurement. The pulse rate is displayed on the pulse display section 7A so that a pulse count is added and the sum of the counts id displayed. Simultaneously, for every pulse, the time from the preceding pulse to the following pulse is displayed on the timer display section 7B in one hundredth of a second intervals. For example, at a pulse rate of twelve pulses per ten seconds, that is when one pulse is generated on the average of every 0.833 seconds, the pulse rate displayed may be, e.g., 83, 84, 83, 82, 85. In case of a person who has an irregular pulse, the pulse rate displayed may be 98, 79, 83, 99, 62, 63.

Next, in order to ensure that the date relating to the irregular pulse is memorized in the microcomputer 6, the memory switch button 8C is depressed. Dates of irregular pulses can be redisplayed from the first to the last by depressing a playback button 8H.

Further, when a fluctuation switch button 8E is depressed, the number of pulses which are shorter than average in one minute is displayed on the timer display section 7B, and the number of pulses which are longer than average in one minute is displayed on the pulse display section 7A. For example, assuming that the number of pulses displayed at the timer display section 7B is 13 and that the number of pulses displayed at the pulse display section 7A is 32. Assuming further that the average pulse is 15, this result shows that a person who has an irregular pulse in fact has a tendency toward delayed pulses.

The above system is explained in more detail in the following.

A fundamental measuring system converts a number of pulses detected for a few seconds into a pulse rate for one minute. The above mentioned pulse rates 83, 84, 83, 82, 85 are pulse rates converted to one minute for respective measurements for one second.

An average determining system calculates an average pulse rate for each measured few second as well as an average for one minute. For example, an average value of the above five pulse rates 83, 84, 83, 82, 85 is 83.4. An average of seven pulse rates of 98, 79, 83, 83, 99, 62, 63 is 81. The number of numerical values larger than a determined average value and the number of numerical values smaller than an average number can be calculated and displayed. For example, in the case of the above discussed average value of 83.4, the number of seconds during measuring is five seconds. During this time, the number of numerical values larger than the average value of 83.4 is two. The number numerical values smaller than the average value of 83.4 (disregarding decimals) is one. However, the calculation of the numerical values is for one minute (sixty seconds). Thus, when numerical values during five seconds of measuring are converted to values for sixty seconds, the number is increased by twelve. That is, the number of numerical values larger than the average value and the number of numerical values smaller than the average value are displayed as 24 and 12, respectively. Accordingly, when irregular pulse rates are measured, they can be measured more accurately by measurement thereof for sixty seconds or longer. For example, during a measurement for sixty seconds, there may be a display indicating that the number of pulse rates larger than an average value and the number of pulse rates smaller than an average value are 13 and 32, respectively. This would indicate to a doctor that that person's pulse is subject to irregular slowed pulses. The doctor then would be able to make more accurate diagnosis and treatment.

The switch mechanism 8 includes a stop switch button 8F for stopping display of the liquid crystal digital display 7 and a clear switch button 8G for clearing the display of the liquid crystal digital display 7. The above procedure is arithmetically computed on the basis of the data stored in the microcomputer 6.

On the other hand, a pen such as a ballpoint pen is incorporated into the second main body section 3. The ballpoint pen comprises a tip 3K, a ballpoint 3B, an ink tube 3D and an ink tube holder 3C. Ink 3J is filled in the ink tube 3D. The ink tube holder 3C has, at the rear end portion thereof, a screw 3G which is engaged with a first projection 3H provided on the first main body section 2. The screw 3G and the first projection 3H jointly constitute a screw mechanism. The ink tube holder 3C also has an engaging member 3F which is engaged with a second projection 3E provided on the second main body section 3.

With the above structure, when the second main body section 3 is rotated with respect to the fixed first main body section 2 in a clockwise direction or a counterclockwise direction, the ink holder 3C is rotated in the same direction as the second main body section 3 through engagement of the engaging member 3F and the second projection 3E. As a result, the ink holder 3C and the ink tube 3D advance or retract by the screw mechanism of the screw 3G and the first projection 3H. When the ballpoint 3B projects from the second main body section 3, the ballpoint pen then is in a condition to write.

Figure 3:
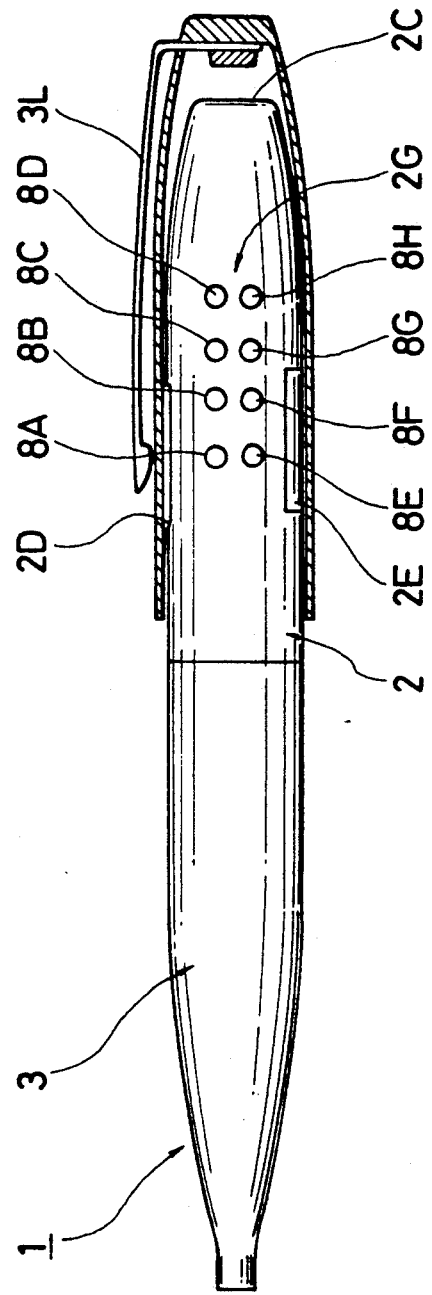
FIG. 3 is a front view of the sphygmometer according to such embodiment of the present invention.

Further, a clip 3L is provided at a forward end of the first main body section 2 as shown in FIG. 3, so that the sphygmometer 1 can be clipped onto a pocket. Therefore, a doctor or a nurse can always carry the sphygmometer 1 which functions both as a sphygmometer and as a ballpoint pen, i.e. he or she can measure the pulse of a patient and write the measurement result at any time.

A further embodiment of the sphygmometer of the present invention will be described with reference to FIG. 4. Since the sphygmometer of FIG. 4 is similar in many respects to that of FIGS. 1-3, common reference numerals are employed, and only differences between the two embodiments will be discussed with regard to FIG. 4.

Figure 4:
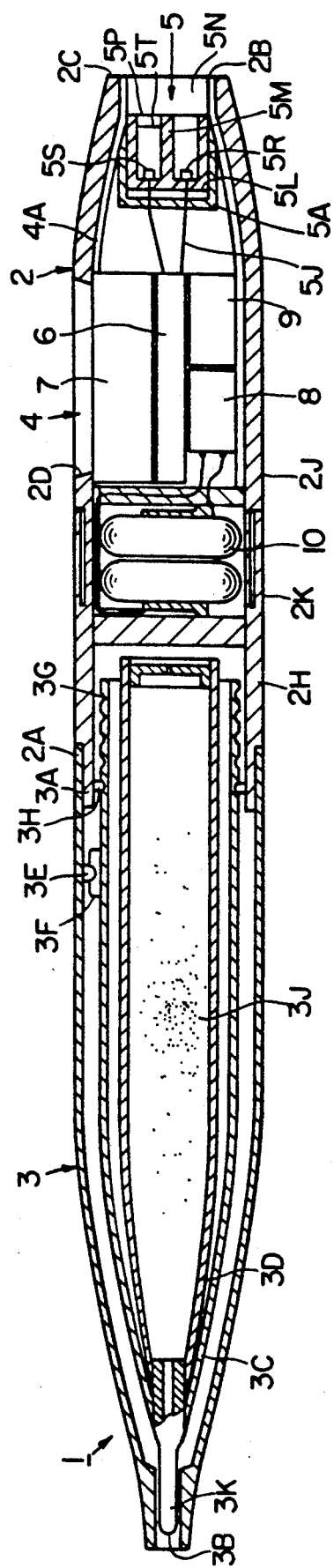
FIG. 4 is a cross-sectional view of a sphygmometer according to another embodiment of the invention.

In FIG. 4, main body measuring section 2 is divided into a main portion 2J and a connection portion 2H by means of a threaded portion 2K. Main portion 2J receives therein pulse measuring device 4 which is formed into a unit by a case or body 4A. A pulse sensor 5 protected by a body 5A is fitted into an extreme outer end of body 4A. In this embodiment, the pulse sensor 5 is in the form of a reflective type infrared photosensor. The photosensor has a structure in which a bottomed cylindrical body 5L is partitioned by a diaphragm or divider 5M into a light emitting portion 5N and a light receiving portion 5P. A light emitting body 5R, for example formed from a GaAs infrared light emitting diode, is disposed in light emitting portion 5N. A light receiving body 5S, for example formed from a silicone phototransistor, is disposed in the light receiving portion 5P, forwardly of which is positioned a visible light filter 5T.

Figure 2:
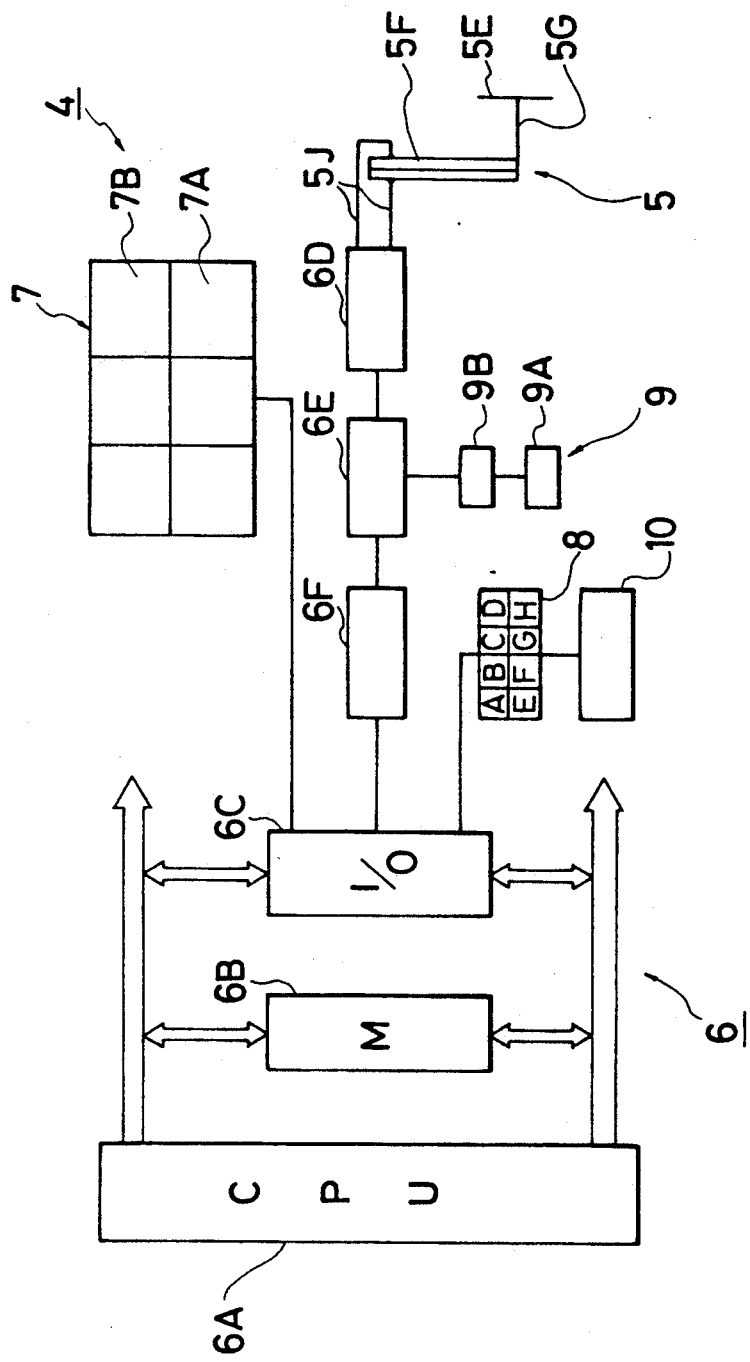
FIG. 2 is a block diagram showing a pulse measuring mechanism of the sphygmometer according to such embodiment of the present invention.

Microcomputer 6, digital display 7 and the like are similar to the elements disclosed and discussed with regard to FIGS. 1-3 However, in FIG. 4 a power source, for example battery 10, is stored at a boundary between the connection portion 2H and the main portion 2J, the power source 10 being capable of being replaced by rotation of threaded portion 2K.

The extreme end of the body 4A is fitted into opening 2B provided at the extreme end of main portion 2J.

The pulse sensor 5 in accordance with this embodiment of the present invention operates in the following manner.

A switch is turned on to apply a constant voltage to pulse sensor 5. Contacting portion 2C is placed in close contact with a body part at which a pulse is to be measured. Infrared rays are irradiated from light emitting body 5R and then are reflected by a blood vessel or artery in the person and are sensed by light receiving body 5S. Since the blood vessel or body has a diameter that varies according to movement of pulses, the amount of infrared rays sensed by light receiving body 5S increases and decreases. The peak of a wave form of such variation is determined to be a pulse, and this is processed by microcomputer 6 in the manner discussed above.

Further, the sphygmometer 1 may display the time at the crystal liquid digital display 7, so that the device also may be used as a clock.

Other types of sensors may be used as the pulse sensor in place of the piezoelectric element or the infrared photosensor. The following are typical types of sensors which may be employed as the pulse sensor:

(a) sensor which utilized a quartz vibrator;

(b) sensor which utilizes a wire resistance strain gauge;

(c) sensor which utilizes a semiconductor capable of detecting pressure;

(d) sensor which utilizes a potential difference. This type of sensor utilizes changes of a potential difference between an electric potential which is generated by the pulse beats of a person whose conducting the pulse rate measurement who acts as ground.

Further, the sensor may be covered by a material forming a cap or a film, whereby the sensor is indirectly contacted with skin covering an artery through the covering material.

According to the sphygmometer of the present invention, the following effects are attainable.

(1) Merely by bringing pulse sensing means of the sphygmometer into contact with skin covering a wristbone artery, a pulse rate per one minute is computed by a microcomputer and digitally displayed. Therefore, the pulse rate can be exactly and easily measured.

(2) Since the overall sphygmometer is compact and portable, it can be always carried by a nurse or a doctor. Therefore, the nurse or doctor easily can measure the pulse rate of an inpatient.

(3) By measuring pulse intervals of a patient using the sphygmometer of the invention, the tendency of such patient to an irregular pulse can be judged exactly.

(4) When the main body is divided into two sections including a pen section having a pen, for example a ballpoint pen, incorporated therein, the device of the invention can be used as a writing instrument by the doctor or nurse.

Although certain preferred embodiments have been shown and described, it should be understood that many changes and modifications may be made thereto without departing from the scope of the invention.

What is claimed is:

1. A sphygmometer device for measuring a pulse rate, said device comprising:

a casing in the form of an elongated cylindrical main body having opposite axial ends, said body being divided into first and second axially spaced body sections;

said first body section having an opening at the respective said main body axial end;

pulse sensing means, positioned within said first body section adjacent said opening and adapted to be brought directly or indirectly into contact with skin covering an artery, for sensing pulses through such artery and for generating signals representative thereof;

display means, within said first body section, for digitally displaying outwardly of said first body section data relating to pulses sensed by said pulse sensing means;

microcomputer means, within said first body section and operatively connected to said pulse sensing means and to said display means, for receiving said signals from said pulse sensing means, for computing a pulse rate per minute based on pulses detected by said pulse sensing means for a period of time different than one minute, and for transmitting to said display means a signal corresponding to said computed pulse rate, such that said display means may digitally display said computed pulse rate; and pen means, positioned within said second body section and operable through the respective main body axial end, for enabling a user of said device to selectively write information relating to data displayed by said display means.

2. A device as claimed in claim 1, wherein said pen means includes a pen point connected to an ink tube.

3. A device as claimed in claim 1, wherein said pen means includes a pen point projectable from and retractable into said second section.

4. A device as claimed in claim 3, further comprising operating means connected to said first and second body sections for enabling projection and retraction of said pen point.

5. A device as claimed in claim 4, wherein said operating means is operable upon relative rotation between said first and second body sections.

6. A device as claimed in claim 1, wherein said pulse sensing means comprises a vibration detector.

7. A device as claimed in claim 6, wherein said vibration detector comprises a piezoelectric element.

8. A device as claimed in claim 1, wherein said pulse sensing means comprises an infrared photosensor.

9. A device as claimed in claim 1, further comprising a battery, positioned removably in said first body section, and operatively connected to said pulse sensing means, said display means and said microcomputer means for powering the same.

10. A device as claimed in claim 1, wherein said microcomputer means includes means for computering a time from a preceding pulse to a following pulse and for transmitting to said display means a signal representative of said computed time.

11. A device as claimed in claim 1, further comprising switch means in said first body section for inputting to said microcomputer means instructions for display of information on said display means.

12. A device as claimed in claim 11, wherein said switch means comprises a first switch for instructing said display means to display pulse rate and a second switch for instructing said display means to display a time from a preceding pulse to a following pulse.

13. A device as claimed in claim 1, further comprising a skin contact member positioned within said opening in said first body section.

14. A device as claimed in claim 1, further comprising a clip on a cap positionable on said casing for enabling said device to be clipped onto clothes of a user.

15. A device as claimed in claim 1, wherein said display means is visible laterally through said casing.

16. A device as claimed in claim 1, wherein said micrcomputer means includes means for computing a mean value of a plurality of said computed pulse rates and a number of said plurality of computed pulse rates higher and/or lower than said mean value, and for transmitting to said display means signals representative thereof, such that said display means may digitally display said computed means value and said number.

* * * * *